(12) United States Patent
Santomassimo et al.

(10) Patent No.: US 7,510,508 B2
(45) Date of Patent: Mar. 31, 2009

(54) USER INTERFACE FOR A RESISTANCE TRAINING DEVICE AND METHOD OF USE

(75) Inventors: Rod N. Santomassimo, Cary, NC (US); Charles Mark Herskowitz, Durham, NC (US); Richard Z. Polidi, Durham, NC (US)

(73) Assignee: Devici, Inc., Durham, NC (US)

( * ) Notice: Subject to any disclaimer, the term of this patent is extended or adjusted under 35 U.S.C. 154(b) by 712 days.

(21) Appl. No.: 10/804,598

(22) Filed: Mar. 19, 2004

(65) Prior Publication Data

US 2005/0209051 A1    Sep. 22, 2005

(51) Int. Cl.
*A63B 21/00* (2006.01)
(52) U.S. Cl. ................... 482/8; 482/1; 482/9
(58) Field of Classification Search ........... 482/1–9, 482/900–902; 434/236, 247; 601/23; 705/2, 705/3
See application file for complete search history.

(56) References Cited

U.S. PATENT DOCUMENTS

| | | | | |
|---|---|---|---|---|
| 5,383,826 A | * | 1/1995 | Michael | 482/3 |
| 5,890,128 A | * | 3/1999 | Diaz et al. | 705/2 |
| 6,558,165 B1 | * | 5/2003 | Curry et al. | 434/236 |
| 6,793,607 B2 | * | 9/2004 | Neil | 482/8 |
| 6,882,955 B1 | * | 4/2005 | Ohlenbusch et al. | 702/160 |
| 7,041,032 B1 | * | 5/2006 | Calvano | 482/4 |
| 7,096,048 B2 | * | 8/2006 | Sanders et al. | 455/569.1 |
| 2006/0223674 A1 | * | 10/2006 | Korkie | 482/8 |
| 2007/0135264 A1 | * | 6/2007 | Rosenberg | 482/8 |

OTHER PUBLICATIONS

Excerpt from WorkoutMan Business Plan created May 2004 by Rod N. Santomassimo to summarize state of art as of the filing of the present patent application, 4 pgs.

* cited by examiner

*Primary Examiner*—Glenn Richman
(74) *Attorney, Agent, or Firm*—The Eclipse Group LLP; Kevin E. Flynn

(57) ABSTRACT

A system, method, and device for recording and tracking resistance training parameters in connection with a resistance training workout. A specially configured portable recording device has a very compact user interface having an input device with very few inputs. A user may record resistance training parameters directly on the recording device both quickly and easily with few and simple keystrokes, resulting in an improved recording process. A personal trainer or strength coach may track the workouts of multiple exercisers with increased convenience. In a particularly preferred embodiment, the recording device is provided in the body of a sport watch.

3 Claims, 14 Drawing Sheets

USER INTERFACE FOR A RESISTANCE TRAINING DEVICE AND METHOD OF USE

FIELD OF THE INVENTION

The present invention relates generally to the field of resistance training.

BACKGROUND OF THE INVENTION

Resistance training, a training method that requires someone to overcome force in movement, is one of the primary methods of improving physical strength, endurance, and power. When performed chronically, this training method has been shown to promote desirable physiological changes including muscle hypertrophy (an increase in muscle size and functional capacity) and an increase in the strength of ligaments, tendons, and bones. Virtually every competitive athlete uses this training method in a manner that is specific to the demands of his or her sport. Others use resistance training for such purposes as improving health and fitness levels, preventing and rehabilitating injuries, altering metabolism, and improving appearance. This training method is a safe form of exercise for the great majority of adults, including many seniors. Resistance training is generally performed with free weights and/or machines. Machine types vary from more traditional versions using iron weights to those using pneumatic cylinders, electromagnetic devices, or elastic structures to provide the resistance.

Muscles advantageously adapt to the loads to which they are subjected. In order to stimulate hypertrophy, muscles generally must be overloaded (subjected to workloads that are greater than normal). Without a sufficient overload, muscle adaptations occur either to a lesser degree or not at all. In order to provide the desired overload and achieve the intended muscle adaptations over the course of a training program, resistance training parameters are frequently varied from one workout to the next during that program. Such parameters may include the exercise intensities (resistance levels), types, frequencies, orders, the number of repetitions in each set of each exercise, and the number of sets of each exercise.

Strength coaches have found periodized weight training to provide many advantages to an exerciser. Periodization is a technique in which the overall training program is divided into multiple phases, e.g., endurance, strength, and power phases, in order to reduce the possibilities of overtraining and staleness and to increase the resistance training stimulus. The overall program is typically designed before it begins, and each phase generally lasts from several weeks to several months. One key to periodization is a relatively frequent variation of resistance training parameters. Each phase of the program generally comprises several different workouts performed cyclically over the duration of that phase. Each workout typically includes exercises selected to train a fraction of the muscle groups of the body, whereby an exerciser completes a cycle of workouts to train all the targeted muscle groups. Multiple sets of multiple repetitions of each exercise are typically performed in each workout. The difficulty of keeping track of the parameters of each workout, particularly as parameters are varied frequently, is evident. At the same time, maintaining accurate records and following the parameters of the prescribed workouts are essential to the success of the training program.

Prior to a workout, "target variables" are preferably determined, e.g., the exercise types, their order, the number of sets, the number of repetitions per set, and the intensity per set for each exercise. During the workout, an exerciser generally attempts to perform the target variables and records information relating to each exercise actually performed. After the workout, the information is tracked and analyzed to design and modify future workouts. While a personal trainer can perform these processes, many exercisers are required to find the time in their already busy schedules to perform the tasks by themselves. Therefore, a desire exists for an easy and efficient method of setting up, displaying, recording, modifying, and tracking workout information.

The most common method of performing such processes is by simply writing a prescribed workout on a page of paper and then recording information on that page during the workout. Such pages are frequently arranged in a spreadsheet format in view of the multiple parameters recorded. Personal trainers, as well as strength coaches of professional and collegiate teams, may list the target exercise variables on the pages with space for exercisers to record the actual parameters performed, and then review the pages frequently to track the progress of each athlete. However, prescribing, reviewing, and analyzing each and every record of each athlete may require substantial amounts of time, particularly, e.g., when responsible for many athletes, when the information is not written clearly by athletes, or when the records are not well organized. Altering the workouts of one or more athletes, such as when the specific demands of an athlete change over the course of a training program because of injury, may be difficult for organizational reasons and may require the preparation of entirely new workout pages incorporating the modified workouts. Moreover, the need to carry a pencil and paper from station to station while training may become an annoyance for an exerciser.

More recently, electronic devices have been developed for similar purposes. For example, U.S. Pat. No. 5,944,633 to Wittrock discloses an electronic hand-held workout tracker. A user may select preset resistance training workouts stored in the memory of the device and may customize such workouts. Alternately, a user may create workouts from scratch on the device. Workout information may be entered onto the device while training and may be uploaded from the device to a personal computer, on which a centralized database may be maintained, for viewing and tracking the workout information at a later date. Physically, the device resembles an electronic calculator or an electronic data organizer. The device may also include an accessory for attaching it to clothing, e.g., a clip that hooks onto clothing or a belt and holster configuration. However, entering the workout information with multiple, complex keystrokes in the middle of an exercise workout may interrupt the rhythm of the workout. The elaborate input (keypad) and display (screen) devices of the user interface may discourage some exercisers from learning how to use the device or from using it on a regular basis while training. The potential exists that the hand-held device may be lost, damaged, or stolen in a training facility, particularly when someone is instead focusing on exercising. As is the case with pencil and paper, carrying the hand-held device from station to station and attempting to store it safely at each station while exercising may similarly become annoying.

U.S. Pat. No. 5,916,063 to Alessandri discloses a system and method for displaying and recording resistance training parameters on resistance training equipment itself, such as directly on traditional selectorized equipment (a type of exercise machine having a stack of iron weight plates to provide the resistance). The Alessandri system incorporates into each machine an electronic unit that communicates with a user-specific tracking device. The tracking device includes a memory device for storing resistance training parameters but has neither an input device nor a display device. In practice, a user instead inserts the tracking device, typically an electronic key, into the electronic unit at each station prior to the exercise. Each machine may incorporate feedback devices to monitor the resistance training parameters (e.g., the number of repetitions) as the exercise is in progress as well as to transfer data back to the electronic key. Alternately, a specially configured monitor at each station may include a user interface for both displaying the values of target parameters and entering information relating to each exercise performed, e.g., with a touch screen. After the workout, the exerciser may use a centralized terminal for bi-directional data transfer with the electronic key. The Alessandri system provides several advantages, such as increasing the convenience for a personal trainer to track the workouts of multiple clients. However, retrofitting the Alessandri system into an existing facility, e.g., by installing an electronic unit into each machine in that facility or by installing altogether new equipment, would be expensive and inconvenient. Only those exercises using such machines may be tracked by the system and therefore by a trainer. Furthermore, someone who regularly exercises in a facility with the Alessandri system but who must on occasion train at a different facility, such as when traveling, may have difficulty remembering the exact parameters for the prescribed workout as well as transferring information of that workout back to the system. Carrying the tracking device from station to station may also become an annoyance.

It would be advantageous to provide a more efficient and less distracting method and device for performing the processes of setting up, displaying, recording, modifying, and analyzing workout information, where such processes may be quickly and conveniently performed regardless of the types and locations of the resistance equipment used.

SUMMARY OF THE INVENTION

The present invention provides many advantageous features in connection with performing such processes. The distraction from recording exercise information while training is decreased. Exercisers are more likely to record exercise information on a regular basis. Personal trainers can easily track the workouts of multiple exercisers. Convenience and ease of use are increased.

In accordance with a preferred embodiment of the invention, an improved recording process requires very few and simple keystrokes by a user to record resistance training parameters as a workout is in progress. The improved recording process increases the ease and speed of recording resistance training parameters on a portable recording device during the workout. The portable recording device has a user interface with only few mechanical inputs or the like (hereinafter "inputs") and with a small display. Therefore, the recording device may be particularly compact, simple, and lightweight. A user may comfortably and securely wear the portable recording device while training and while entering information thereon. The risks of loss, damage, and theft are decreased. The annoyance of carrying a hand-held device from station to station is eliminated. The need to insert a tracking device into a unit at each station is also eliminated. The present invention may be used in connection with virtually any resistance training exercise regardless of equipment and location. The invention may be mass produced with excellent economy.

In accordance with a preferred embodiment of the invention, an improved program flow includes a workout routine that may be executed on a portable and particularly compact recording device. Such routines as designing, analyzing, and modifying workouts may be executed on a separate interface such as a personal computer or the like. The program flow facilitates execution of the latter processes by permitting the use of a computer monitor, keyboard, mouse, and the like to view and enter information in connection therewith. However, in accord with an important feature of the invention, the workout routine simplifies the process of recording the resistance training parameters, requiring simple and few, if any, keystrokes during a workout. The workout routine may be executed with few inputs and a small display, allowing the portable recording device to be very compact, allowing the characters on the display to remain large and legible for easy viewing, and allowing the inputs to remain large for simple actuation.

In accordance with preferred embodiments of the invention, a user may enter resistance training parameters particularly quickly and easily in order to minimize any interruption to a workout. In one such embodiment, the workout routine may require only a single keystroke between exercise sets as long as target variables are met, further reducing any interruption to the workout. In another such embodiment, the workout routine may require no keystroke at all while recording resistance training parameters between sets, eliminating virtually all distaction while helping an exerciser maintain a desired pace in the prescribed workout.

In accordance with a particularly preferred embodiment of the present invention and because of the improved program flow and simplified user interface of the recording device, all the functionality of the recording device may be provided in the body or housing of a digital sport wristwatch or the like. A sport wristwatch (hereinafter "sport watch") is generally configured to be durable, comfortable, and lightweight. It has a simple user interface, including few (and relatively large) inputs and large characters, for ease of use during an athletic activity. Such an embodiment is feasible in the present invention because, in contrast with prior art resistance training devices which require more elaborate and often cumbersome user interfaces, the present recording device may have a very simple and compact user interface. The sport watch advantageously remains securely fastened to the wrist as a workout is in progress. The characters may be easily viewed and the inputs may be easily actuated without removing the watch from the wrist (in contrast with many "clip-on" devices). The present sport watch is very convenient to use and is less likely to be lost or damaged than a hand-held device.

Of particular advantage, the program flow of a preferred embodiment of the present invention may be incorporated into an existing sport watch having few inputs and a compact display without any physical modification to the body of the watch. The manufacturing process may be simplified because existing manufacturing equipment (molds, tooling, etc.), and even existing watch bodies themselves, may be used. The recording device of the present invention may also be very inconspicuous because it may lack any additional physical structures or encumbrances that might otherwise decrease the attractiveness, comfort, or desirability of the sport watch. The sport watch would preferably have the capacity to communicate with a personal computer or the like for transferring resistance training information to and from the computer, permitting workouts to be set up, analyzed, and modified on the computer. Further features and advantages of the invention will become apparent from the detailed description in connection with the following figures.

BRIEF DESCRIPTIONS OF THE DRAWINGS

For a complete understanding of the above and other features of the invention, reference is made to the following detailed description and the accompanying drawings, wherein:

FIGS. 5A and 5B are flow diagrams illustrating a preferred program flow corresponding to a setup routine of the present invention, wherein a user may design a workout by executing the setup routine on a personal computer or the like.

FIG. 6 is a flow diagram illustrating a preferred program flow corresponding to the transfer of data between a recording device of the present invention and a personal computer or the like.

DETAILED DESCRIPTIONS OF THE PREFERRED EMBODIMENTS

Figure 1A:
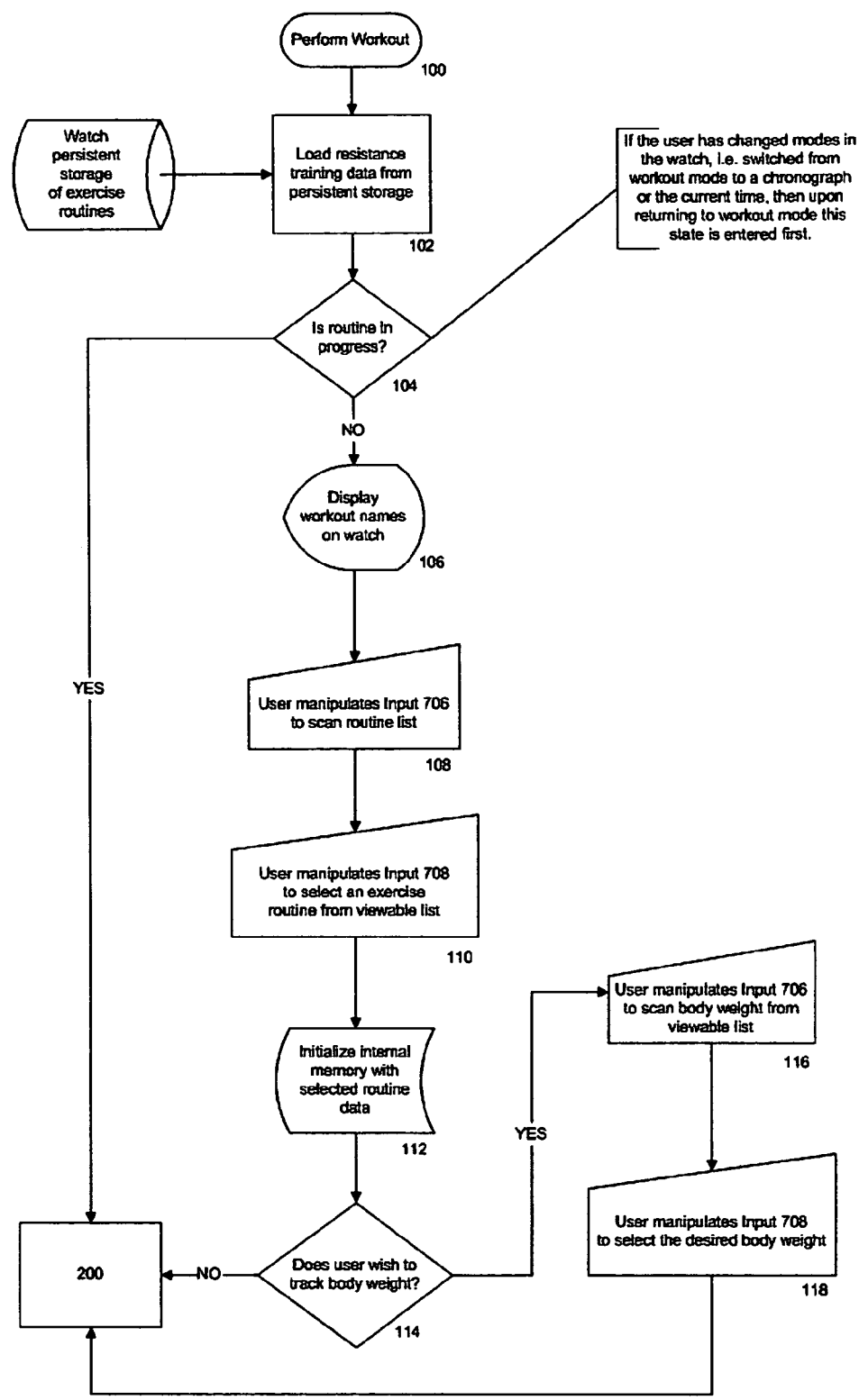
FIG. 1A is a flow diagram illustrating a preferred setup segment of a workout routine of the present invention.

In accordance with a preferred embodiment of the present invention, an improved process of recording resistance training parameters is enabled. A user may perform the recording process easily and quickly on a portable recording device that has a very simple user interface. The recording device preferably, although not necessarily, may be incorporated into the body of a sport watch. A program flow that preferably includes a specially configured workout routine (or workout mode) enables the improved recording process. A user records resistance training parameters while executing the workout routine on the portable recording device during a workout.

The preferred logic of the workout routine has been developed to allow a user to enter resistance training parameters and the like with improved speed and simplicity. For example, the preferred logic does not require a user to select each exercise manually prior to recording the respective parameters for that exercise. The logic does not require a user to enter the value of each parameter manually, e.g., on a numeric keypad, after completing each set, further increasing the speed of recording such parameters. The logic preferably obviates the need to display menus, exercise lists, spreadsheets and the like, which would otherwise require a user interface having a larger and more elaborate display and would probably add complexity to the recording process. Instead, the display only needs to be sufficient to show the exercise parameters of a single set of a single exercise. At the same time, the logic allows the recording device and process to be particularly user friendly, easy to learn, and easy to use on a regular basis.

In a preferred embodiment, the logic of the workout routine flows automatically from one set to the next, whereby a user is only required to enter the value of a resistance training parameter if the target value is not performed. Otherwise, the user only must confirm the target parameters (e.g., exercise weight and number of repetitions) with a simple keystroke. The user or a trainer preferably determines the target parameters prior to the workout on a separate interface such as a personal computer or the like. After confirmation of the parameters, the logic automatically displays the target variables for the subsequent set of the workout, whether the subsequent set is for the same or a next exercise. The user preferably determines the exercise order prior to the workout on the separate interface to enable the improved and expedited recording process of the present invention.

A preferred workout routine of the program flow enables a user to execute the entire routine with very few keystrokes and by means of few mechanical inputs. An exerciser preferably uses no more than two such inputs while a workout is in progress. One of the two inputs preferably comprises a pushbutton. The second input preferably comprises a rotating device, e.g., a knob or crown, which may be easily turned in either of two directions to provide a bi-directional input. It is contemplated that one or both of the inputs may alternately comprise a touch-screen device or the like, may instead be actuated by voice, or may comprise any of the many other available input devices. In addition to requiring few inputs, the workout routine may be executed with the use of a small display, preferably a liquid crystal display or the like having a surface area less than one square inch. Simultaneously, the user interface may display relatively large characters (numbers and/or letters) in a manner that is easy for a user to view and understand. The text may be displayed in any language with the corresponding characters. The term "display" is used herein to reference the portions of the screen for displaying digital characters and other digital graphics.

Figure 1B:
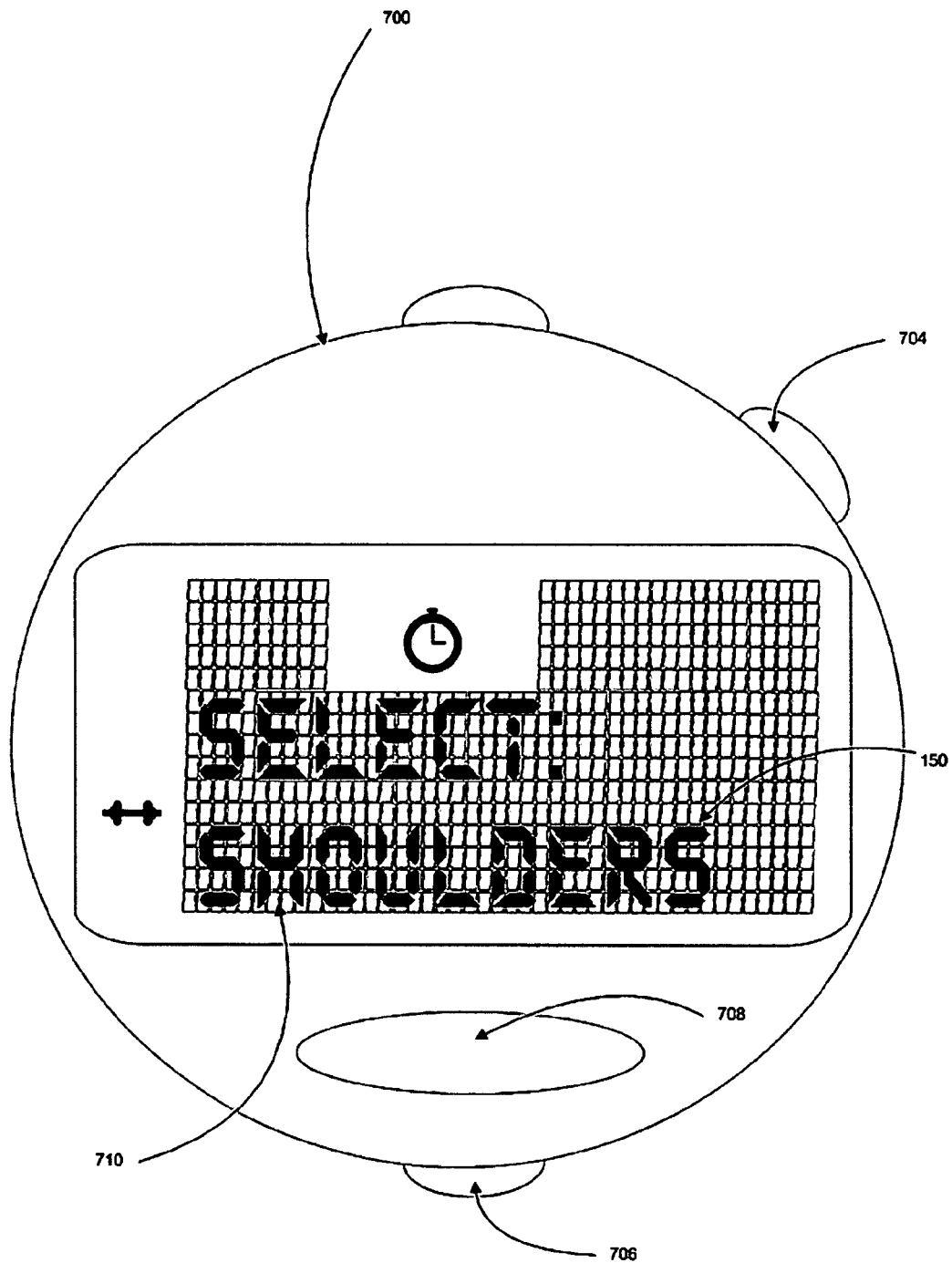
FIG. 1B is a top view of a preferred embodiment of a user interface of the present invention having a display corresponding to step 106 of FIG. 1A, where the display shows the name of one of the workouts.

While a user trains, the recording device executes the workout routine of the program flow. The logic of a setup segment of a first preferred embodiment of the workout routine is shown in FIG. 1A. A user interface corresponding to the setup segment of the workout routine is shown in FIG. 1B. A user typically enters the workout mode of the program flow immediately prior to beginning a workout by actuating a separate mode button 704, causing the logic to initiate at step 100. Workout data is immediately loaded from the persistent storage of the recording device in step 102, and the logic determines whether a routine is already in progress in step 104. A routine may already be in progress, e.g., if a user earlier exited the workout routine midstream and subsequently reentered it. If a routine is not already in progress, the logic proceeds to step 106, where it displays on the recording device a single workout name from a list of workout names. The logic preferably automatically displays the workout scheduled for the present day, where the recording device has means to track the current day, month, and year for determining the respective workout. In addition, two or more workouts may be scheduled for a single day, e.g., one in the morning and the other at night, whereby an internal clock of the recording device is used to determine which of those workouts to display.

An example of a user interface having a display corresponding to step 106 is shown in FIG. 1B, where the user interface is referred to generally by the reference numeral 700. The user interface 700 is here displaying a workout 150 named "SHOULDERS." Of particular advantage, because the display 710 of the user interface 700 shows only the name of a single workout, the text may be large and thus easily viewed without requiring a large display. In a preferred embodiment, the workout name may also scroll across the display from right to left, particularly if the name is long. By manipulating the rotating device 706, the user may select a workout different than the one displayed (step 108). The user then confirms the workout in step 110 by pressing the push-button 708. Upon confirmation, the logic initializes internal memory with data of the selected workout in step 112. The logic next determines whether the user wishes to track his or her body weight in step 114. If so, the logic preferably displays the body weight from persistent storage. The user manipulates the rotating device 706 in step 116 to set the current body weight and then presses the push-button 708 in step 118 to confirm. Then, in step 200, the logic reads the exercise name, the set count, the exercise weight, and the number of repetitions for the next exercise from the persistent storage of exercise data for the selected workout. If the user does not wish to track body weight, the logic skips directly to step 200 to read the resistance training parameters.

Figure 2A:
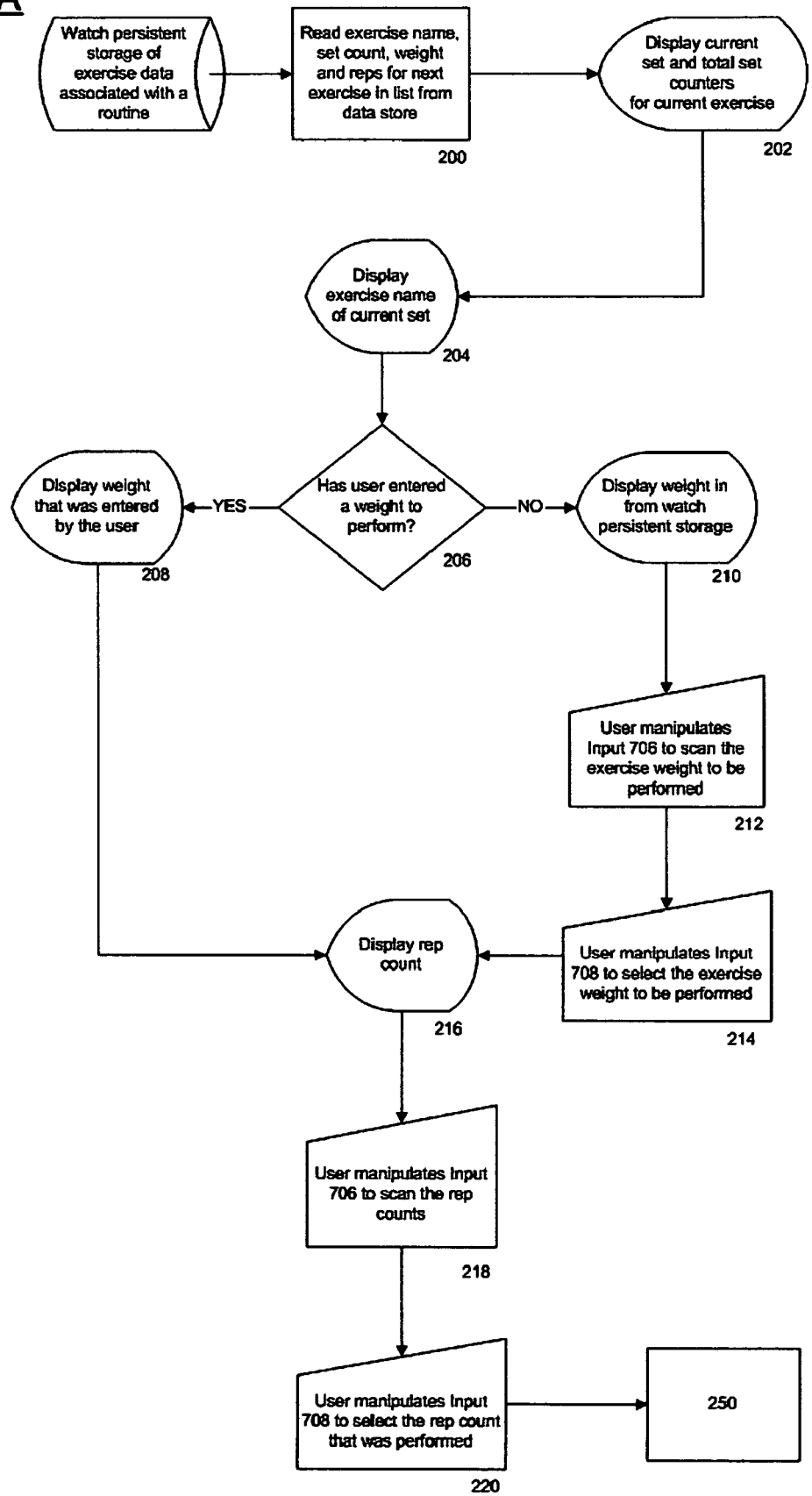
FIGS. 2A and 2B are flow diagrams illustrating a first preferred program flow corresponding to a data entry segment of a workout routine of the present invention.
Figure 2B:
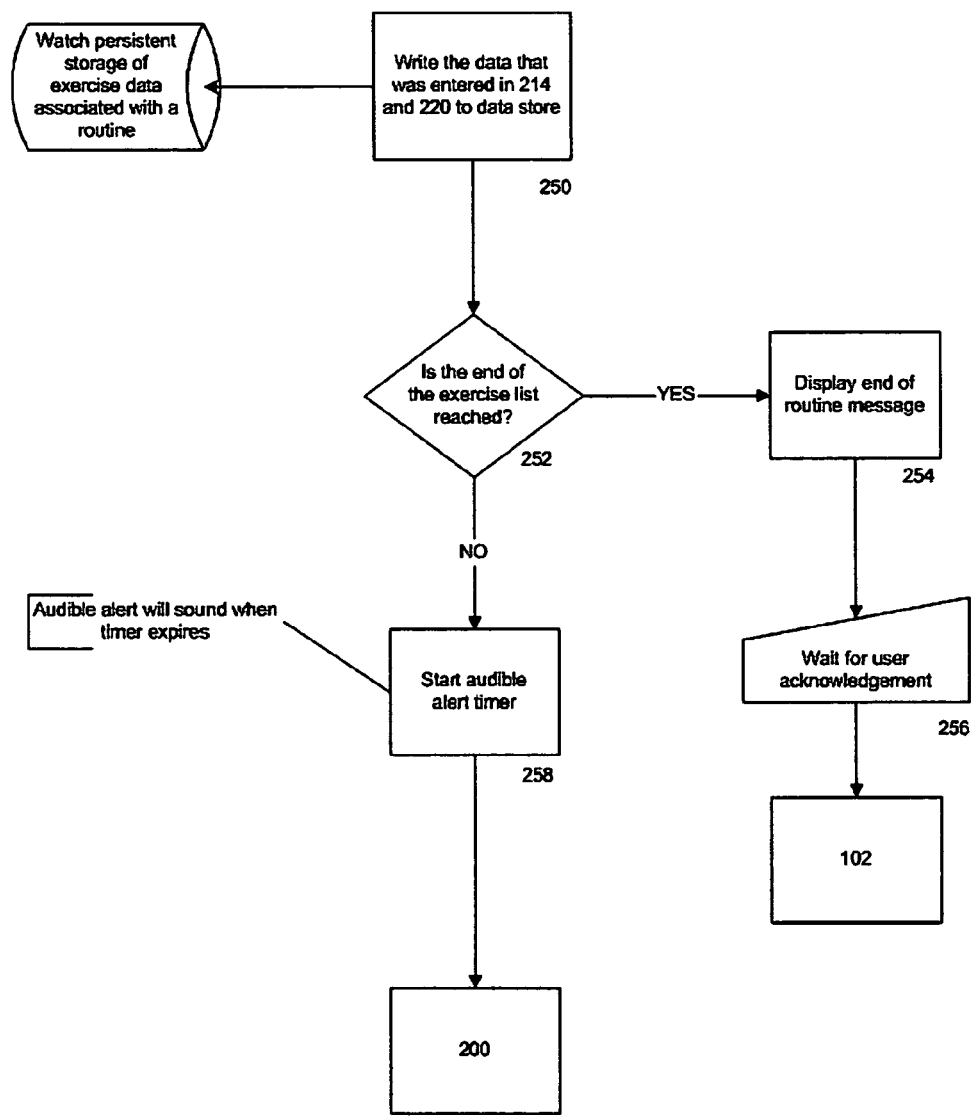
Figure 2C:
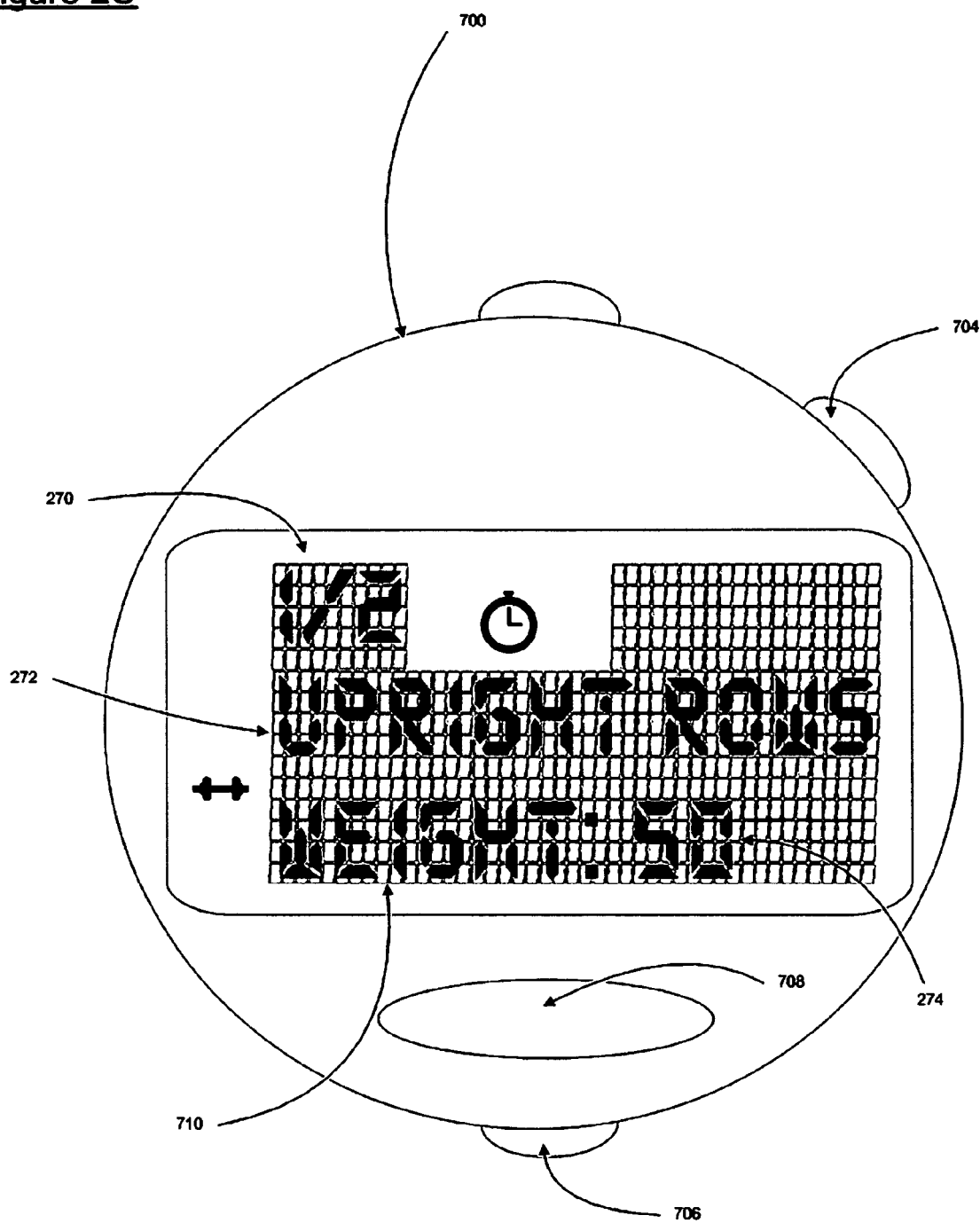
FIG. 2C is a top view of a preferred embodiment of a user interface of the present invention having a display corresponding to step 208/210 of FIG. 2A, where the display shows the set count, exercise name, and exercise weight.

The logic of a data entry segment of a first preferred embodiment of the workout routine is illustrated in FIGS. 2A and 2B. After step 200, the logic next displays the current set and total set count for the current exercise in step 202, as well as the exercise name in step 204. In step 206, the logic determines whether the user earlier entered an exercise weight. If the user has already entered an exercise weight, e.g., prior to exiting and then re-entering the workout mode, then the logic also displays that weight in step 208. Otherwise, the logic displays the exercise weight from persistent storage in step 210. As shown in FIG. 2C, the user interface 700 of the present invention preferably displays all the information from steps 202, 204, and 208/210 on a single display at one time in a simple and straightforward format with characters which are easily viewed. The set count 270 is set number one out of two sets. The exercise name 272 is "UPRIGHT ROWS." The exercise weight 274 is fifty pounds and, in a preferred embodiment, may be flashing to indicate that it may be varied. The exercise weight 274 may additionally be displayed in alternate units, e.g., kilograms. The user may manipulate the rotating device 706 to scan the exercise weight to be performed in step 212. For example, a clockwise rotation is used to increase the value of the exercise weight, and a counter-clockwise rotation is used to decrease the value. Each incremental rotation of the rotating device 706 preferably causes a variation of exercise weight by five pounds. The incremental changes may instead be set to a different amount by the user or the manufacturer. For example, a one pound increment or two and a half pound increment may be used to scan lighter exercise weights, while a five pound or ten pound increment may be used to scan heavier exercise weights. The user then confirms the exercise weight in step 214 with a single keystroke of the push-button 708.

Figure 2D:
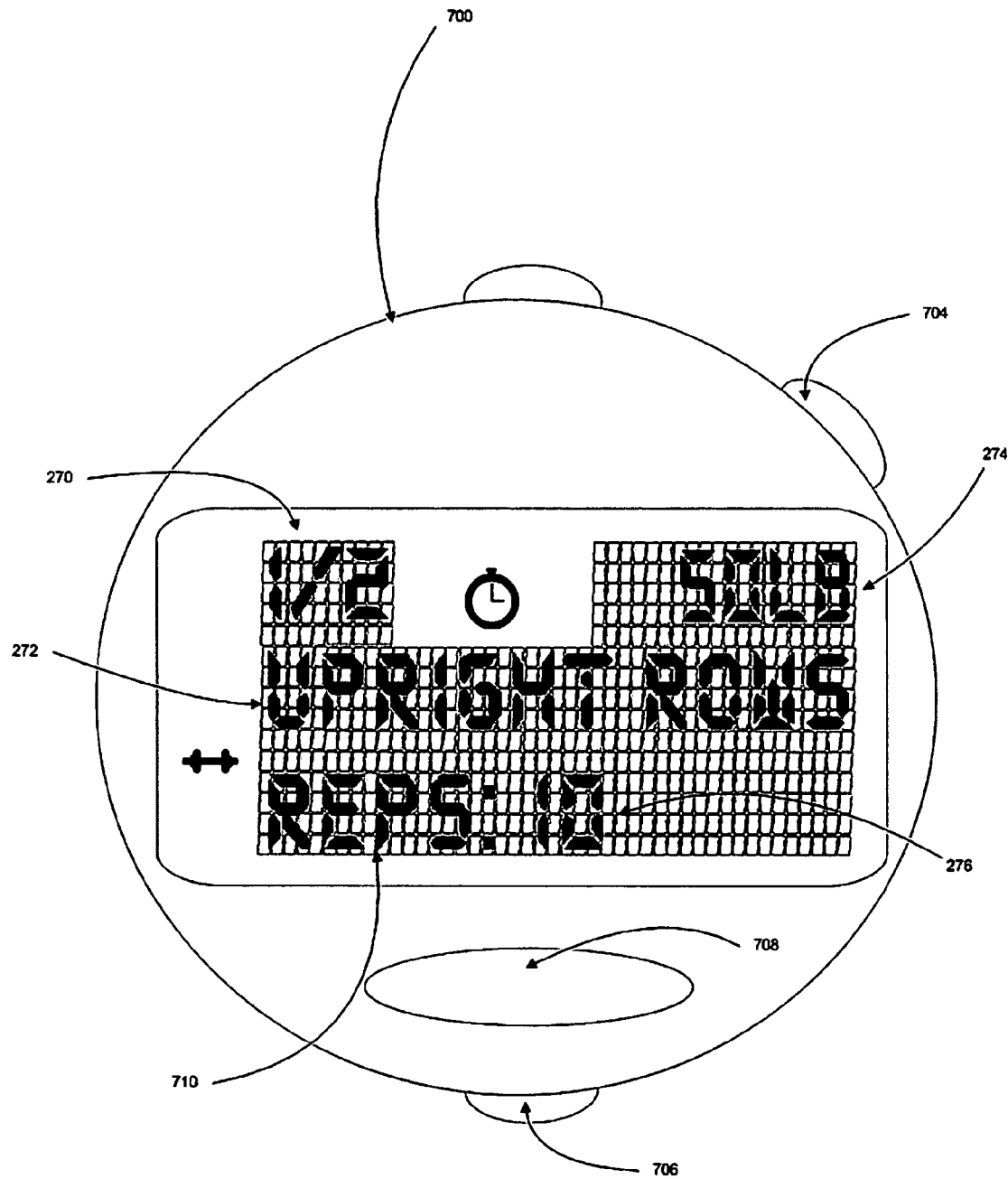
FIG. 2D is a top view of a preferred embodiment of a user interface of the present invention having a display corresponding to step 216 of FIG. 2A, where the display shows the set count, exercise name, exercise weight, and repetition count.

The logic next displays, and preferably flashes, the number of repetitions in step 216. As shown in FIG. 2D, the user interface 700 advantageously displays all the information from steps 202, 204, and 208/210, and 216 on a single screen at one time, in a similarly simple and straightforward format. Distinctions between the displays of FIGS. 2C and 2D preferably include only whether the repetition count 276 is shown (ten repetitions are shown in FIG. 2D) and the location where the exercise weight 274 is shown. It can be appreciated that the display may be relatively small without detracting from its clarity, ease of viewing, or ease of use. At this point in the workout routine, it is expected that the user perform the selected exercise. Upon completion, the user either confirms that the target number of repetitions was completed (step 220) by pressing the push-button 708 or uses the rotating device 706 to vary the number of repetitions to match the number completed in step 218 before confirming with the push-button 708 in step 220.

It is further contemplated that, in an alternate embodiment, a user may vary the exercise name directly on the recording device. For example, in such an embodiment a user may press and hold the push-button 708 at any time between steps 210 and 216 and then manipulate the rotating device 706 to scan different exercises from the same workout routine. Pressing and holding the push-button 708 a second time would confirm the selection and return the logic to the same point where it left, resuming the routine where it left.

In step 250, the logic writes the data entered in steps 214 and 220 to persistent storage associated with the respective workout. If the logic determines that the final set of the final exercise is not reached in step 252, then it cycles back to the step 200 of reading the parameters (exercise name, set count, exercise weight, and number of repetitions) for the subsequent set, whether that set is of the same or of the next exercise of the workout. The logic then follows a similar flow for each set of each exercise in the respective workout. Upon reaching the final set, the logic displays an end-of-routine message in step 254 and requests user acknowledgment in step 256, e.g., by pressing the push-button 708. The logic next returns to the step 102 of loading exercise workouts from storage, displaying the name of the subsequent workout to be performed in the respective training program.

As shown in FIG. 2B, the logic may also include an audible alert timer for notifying a user of a pre-selected amount of rest between exercise sets. The amount of rest between sets is an additional resistance training parameter that may be varied in an attempt to increase the exercise stimulus. Some phases of an overall training program may require less rest while other phases require more in order to optimize the intended results. The amount of rest between sets may also be varied at different points of the same workout. An audible timer may been incorporated into the program flow of a preferred embodiment of the present invention, as shown in step 258, in order to enable a user to keep track of the amount of rest between sets with greater accuracy. The timer preferably reads preset rest times from persistent memory at the same time it reads the values of other resistance training parameters. Immediately after the user confirms the number of repetitions performed in a given set in step 220, the timer begins to run. When the timer reaches the prescribed value, the alarm chirps to inform the user to begin the next set. It is also contemplated that the alarm may incorporate a device to cause the recording device to vibrate or to emit another non-audible signal, rather than emit an audible signal, in order to be less conspicuous to others nearby. The timer begins and runs similarly for each subsequent set until the final set of the routine.

In accordance with a second preferred embodiment of the workout routine of the present invention, the program flow may advantageously require only a single keystroke between sets. With only a single actuation of a single input, preferably of the push-button 708, a user may both confirm multiple resistance training parameters for a set and cause the logic to display the parameters for the following set. The present configuration results in additional ease of use and even less distraction from recording variables when training.

Figure 3A:
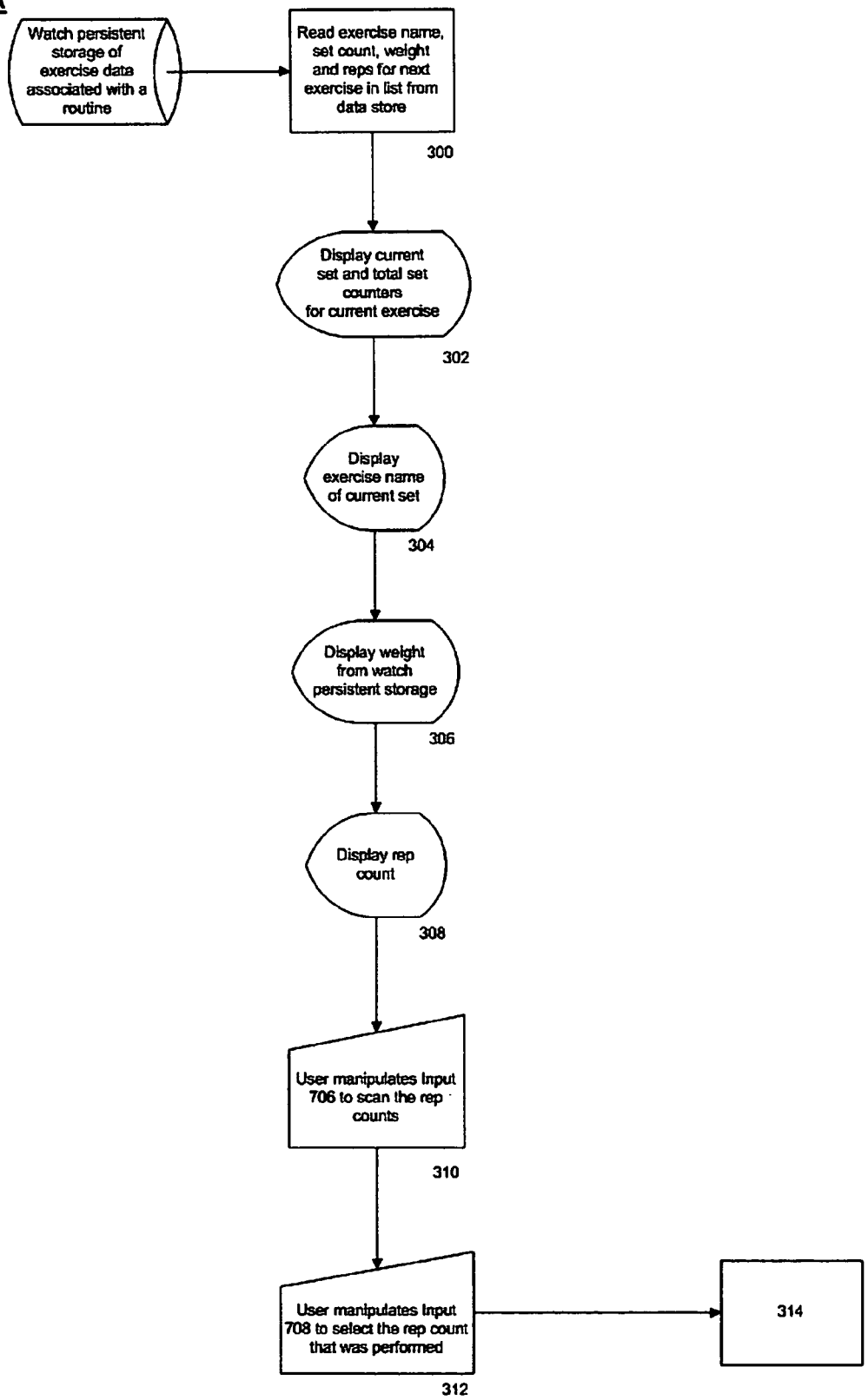
FIGS. 3A and 3B are flow diagrams illustrating a second preferred program flow of a data entry segment of a workout routine of the present invention, wherein the program flow may require only a single input between exercises.
Figure 3B:
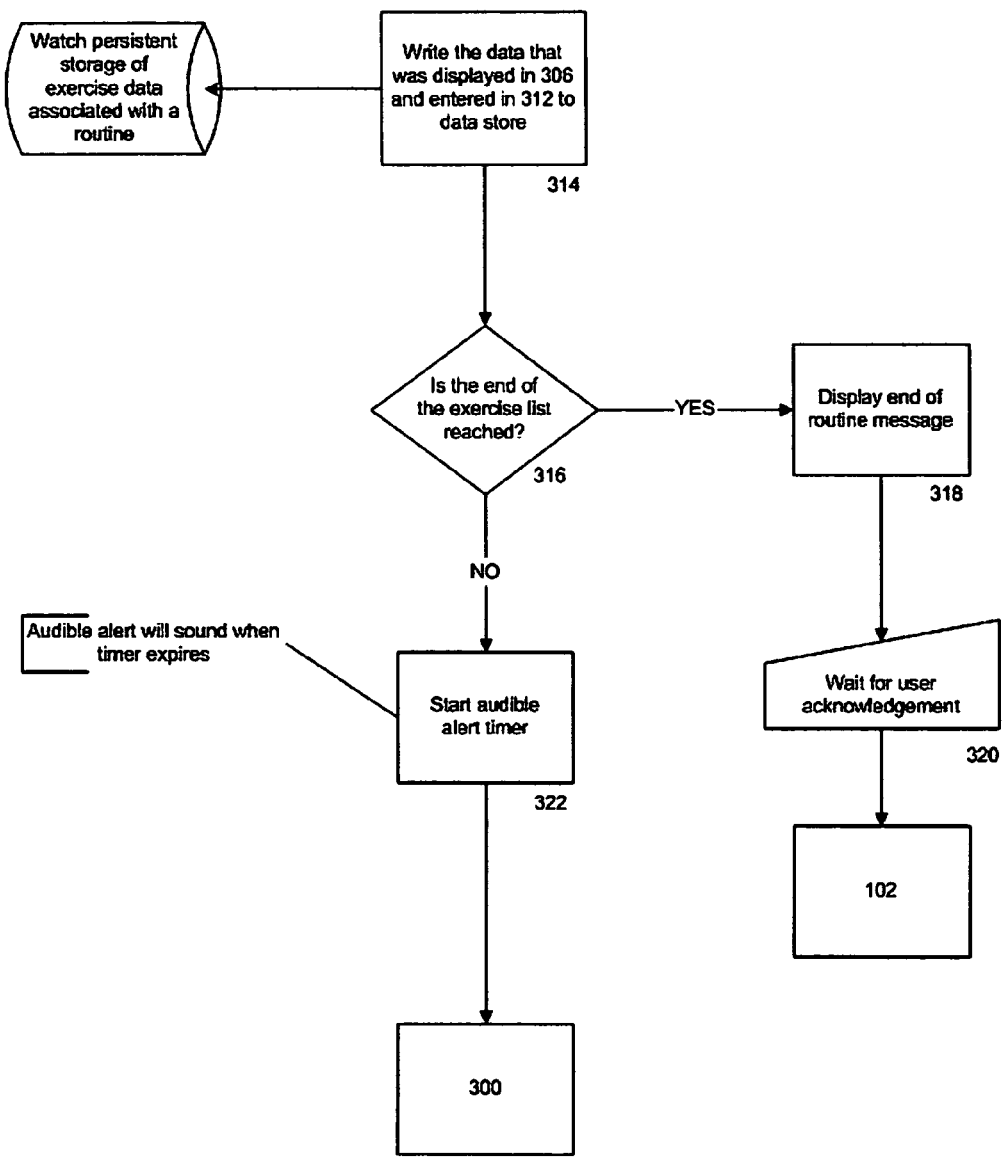

The logic and execution of the second preferred embodiment of the workout routine are illustrated in FIGS. 1A, 3A, and 3B. Upon entering the workout mode, typically immediately before beginning a workout, the logic follows steps 100-118 in FIG. 1A, discussed above. The logic next moves to step 300 in FIG. 3A rather than to step 200. In step 300, the logic reads such parameters as the exercise name, set count, exercise weights, and number of repetitions from the persistent storage of the recording device. In accordance with the second preferred embodiment, the logic next displays, all on the same screen rather than requiring a user to sequence through screens, the exercise name, the current set and total set counters (e.g., set 1 of 3), the exercise weight, and the target number of repetitions, as shown in steps 302, 304, 306, and 308. The user interface 700 corresponding to those steps may be virtually identical to that shown in FIG. 2D.

At this point, it is expected that the user perform the exercise. As long as the target repetition count is reached with the prescribed exercise weight, a user only needs to press the push-button 708 in step 312 to confirm the parameters. The logic then immediately writes the values of the parameters to persistent storage in step 314 and initiates the audible (or vibrating) alert timer in step 322 as long as the final set of the final exercise is not reached. If the target repetition count is not met or its value otherwise requires changing, a user may modify its values in step 310 with the rotating device 706. It is also contemplated that, if needed, a user may vary another parameter, such as the exercise weight or exercise name, by first pressing and holding the push-button 708 and then manipulating the rotating device 706 to vary the respective parameter. In such an embodiment, the push-button 708 would preferably also be used to move sequentially from one parameter to the next in order to change the respective parameter. Pressing and holding the push-button 708 a second time would return the logic to the same point where it left and would resume the routine. The remainder of the logic is virtually identical to that of the first embodiment of the workout routine, discussed above.

In accordance with a third preferred program flow of the workout routine, the logic may move through an entire workout without requiring any keystroke whatever by a user. As long as the user completes the prescribed exercises and the target parameters, the logic moves automatically from one set to the next without requiring the user to actuate any inputs at all. The logic also allows prescribed rests between sets. This embodiment advantageously eliminates virtually all distraction while also helping to guide an exerciser through a workout at a desired pace, determined and set by the user.

Figure 4:
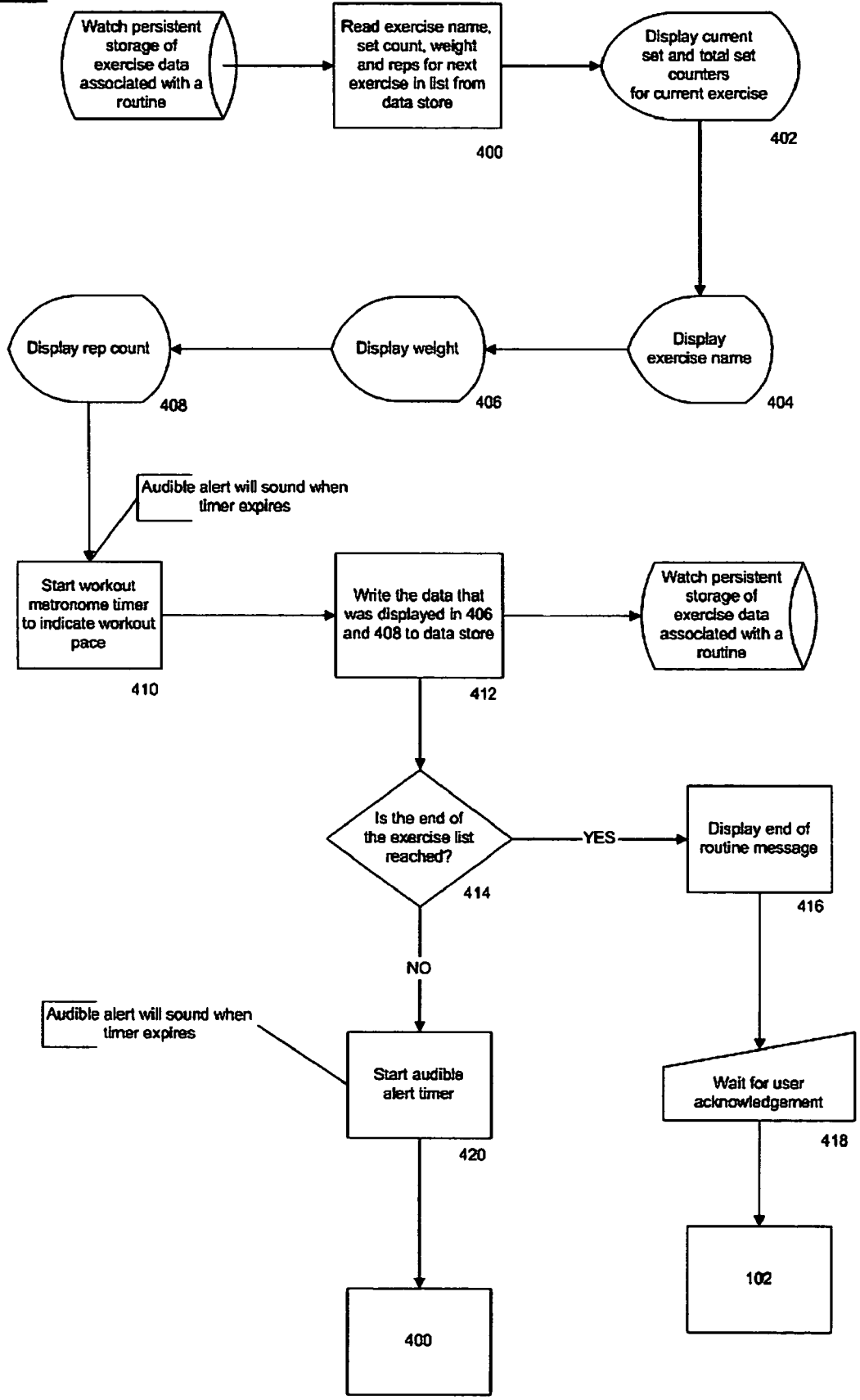
FIG. 4 is a flow diagram illustrating a third preferred program flow of a data entry segment of a workout routine of the present invention, wherein the program flow may require no input between exercises.

The logic and execution of the third preferred program flow are illustrated in FIGS. 1A and 4. Upon entering the workout mode of the program flow, typically immediately prior to beginning a workout, the logic follows steps 100-118 in FIG. 1A (discussed above), moving next to step 400 in FIG. 4 rather than to step 200. In step 400, the logic reads such parameters as the exercise name, set count, exercise weights, and number of repetitions. In accordance with the third preferred embodiment, the logic next displays, all on the same screen, the exercise name, the current set and total set counters (e.g., set 1 of 3), the exercise weight, and the target number of repetitions, as shown in steps 402, 404, 406, and 408. The user interface 700 corresponding to those steps may be virtually identical to that shown in FIG. 2D. At this point, the logic initiates a metronome timer in step 410 corresponding to the prescribed amount of time for performing the set. The user preferably determines the attributes of the timer prior to the workout on a separate interface.

At this point, the user performs the exercise. As long as the target repetition count is reached with the prescribed exercise weight in the prescribed time period, no keystroke at all is required to confirm that all the parameters are accurate. The logic then immediately writes the values of the parameters to persistent storage in step 412 and determines whether the final set of the final exercise is reached in step 414. If not, the logic initiates the audible (or vibrating) alert timer in step 420 and returns to step 400 for the subsequent set. If the final set is reached, the logic displays the end of routine message in step 416, waits for user acknowledgment in step 418, and returns to the step 102 of loading exercise workouts from storage, displaying the name of the subsequent workout to be performed in the respective training program. If a user wishes to pause a workout, since the workout in this embodiment is timed, it is contemplated that the user may pause the routine by pressing push-button 708. In addition, if the target variables are not met or if their values otherwise require changing, it is contemplated that a user may vary a parameter, such as the repetition count, exercise weight, or exercise name, by first pausing the routine with the push-button 708 and then manipulating the rotating device 706 to vary the respective parameter. In such an embodiment, the push-button 708 would preferably be used to move from one parameter to the next in order to change the desired parameter. For example, pressing the push-button 708 a first time would both pause the routine and permit the user to vary the repetition count. Pressing a second time would permit the user to vary the exercise weight. Pressing a third time would permit the user to vary the exercise name. Pressing a fourth time would return to the same point in the logic where it left and would resume the routine.

It can be appreciated that the program flow in each of the three foregoing embodiments requires simple and few, if any, keystrokes to record resistance training parameters for virtually any resistance training workout. In each embodiment, the workout routine requires the use of only two inputs to execute the routine, namely the crown 706 and push-button 708. There is little, if any, interruption between sets to enter the parameters. The workout routine moves exceptionally quickly and easily from one set to the next, enabling the improved recording process. A user is not required to select each exercise on the device as it is performed because the order is preset and the routine automatically displays each exercise in order. Preferred embodiments of the user interface 700 of the recording device advantageously do not require an alphanumeric keypad, nor do they even require a numeric keypad. The screen of the recording device preferably does not display menus, lists, spreadsheets, or the like at any one time. Therefore the display may be compact, e.g., having a surface area (for displaying characters) preferably less than one square inch, and in some embodiments less than one-half square inch or even less than one-quarter square inch. Preferably the display is approximately one-half inch in height and one inch in width. Thus the overall interface 700 may be particularly compact as well.

In accordance with a preferred embodiment of the present invention, a personal computer may be used to provide an interface for setting up, modifying, and tracking workouts.

The larger display and an input device (including a monitor, keyboard, mouse, etc.) of a personal computer facilitate those processes. Performing the steps on the recording device instead would be less convenient.

Figure 5A:
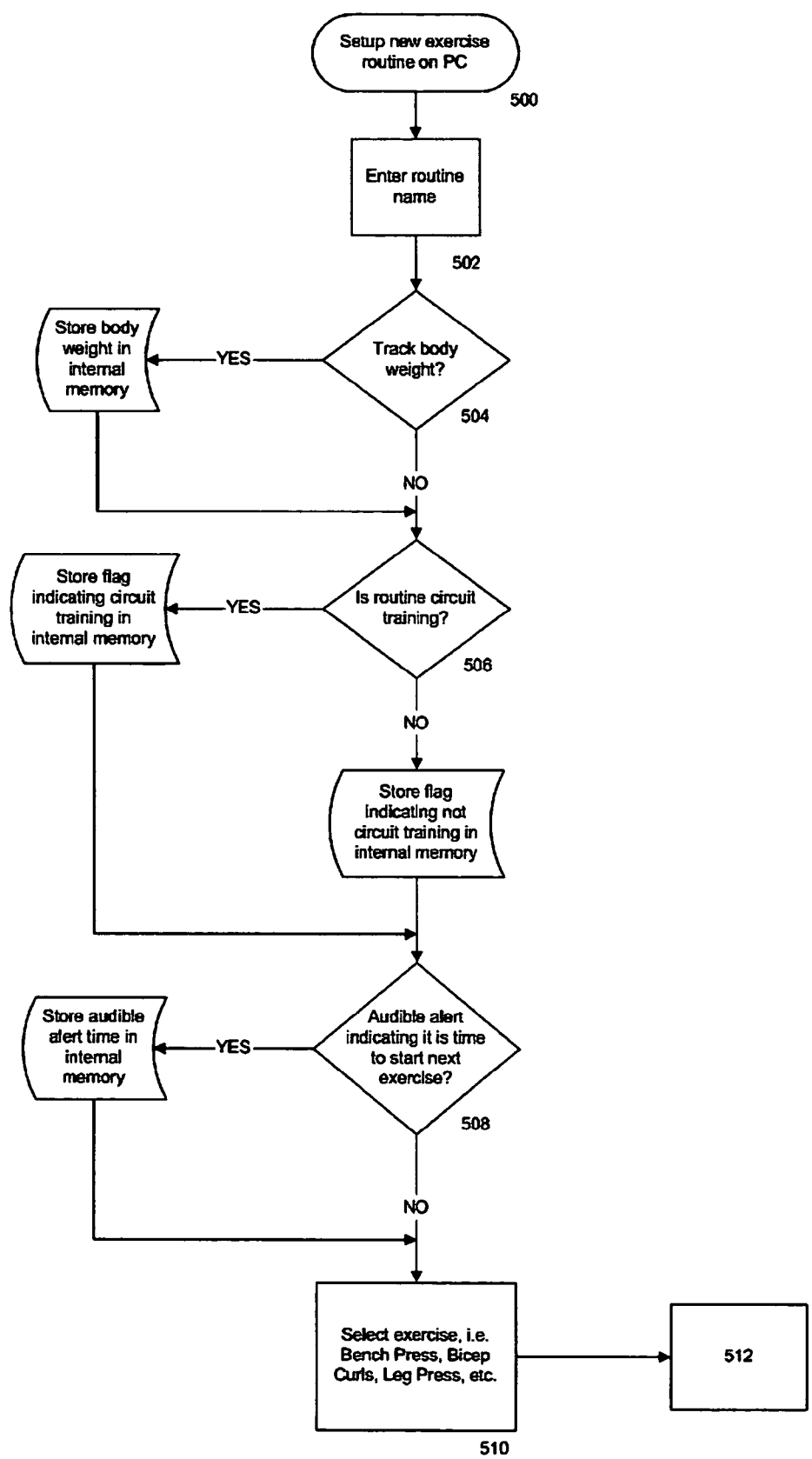
Figure 5B:
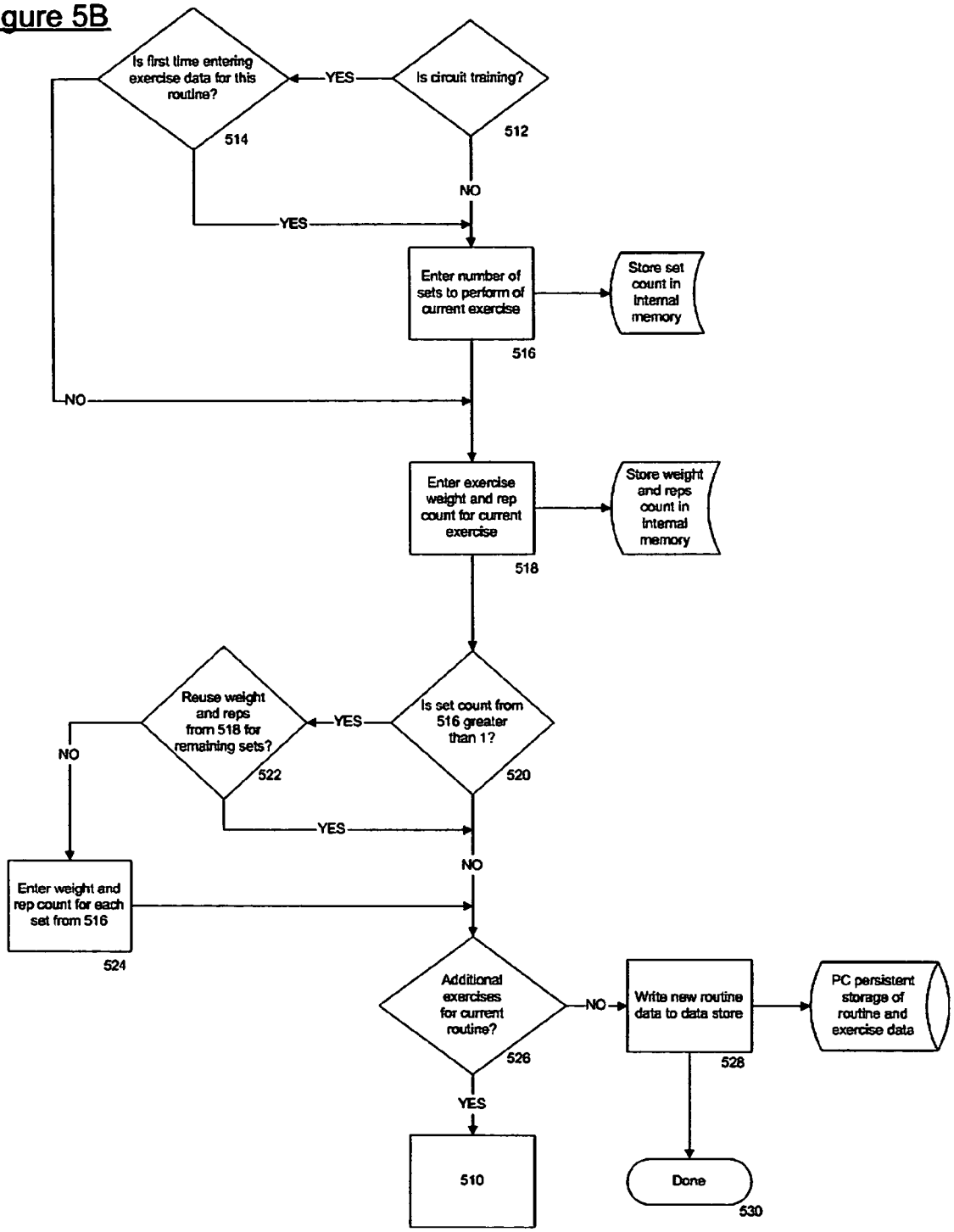

One example of a preferred setup routine or "setup mode" of the overall program flow is shown in FIGS. 5A and 5B. Upon entering the setup routine, preferably on a separate interface such as a personal computer, a user enters the logic at step 500. The logic prompts the user to enter a workout name in step 502. The user is then asked whether to track body weight in step 504. If so, the user preferably enters his current body weight to provide a benchmark for future reference, and the logic stores the relevant body weight information and flags in internal memory. If the user indicates that she does not want to track body weight, the logic flows directly to step 506. In step 506, the user is asked whether the new workout comprises circuit training. If so, the logic stores a circuit training flag into internal memory. Otherwise, the logic stores a flag indicating the workout does not comprise circuit training. In step 508, the user is asked whether an audible alert should be provided between sets. If so, the user enters the desired rest times, and the logic stores that data into its internal memory. If not, the logic flows directly to step 510. In step 510, the logic prompts the user to select a specific exercise from a list. The user is preferably also given an opportunity to enter an exercise name, e.g., with a keyboard of the personal computer, if the exercise name does not appear on the list.

For each exercise, the logic determines in step 512, based on the internal flag, whether the exercise is part of a circuit training workout. If so, the logic determines whether data has been entered before for the workout in step 514. If it is the first time entering data, the logic prompts the user to enter the number of sets of the exercise in step 516 and stores that data in internal memory. The logic next prompts the user to enter the exercise weight and repetition count per set in step 518 and stores that data in internal memory. If not the first time entering data for the circuit training workout, the logic skips to step 518. If the exercise is not part of a circuit training workout, then the logic flows directly to step 516. In step 520, the logic determines whether the set count which was entered in step 516 is greater than 1. If so, the user is questioned in step 522 whether to use the same weight and perform the same number of repetitions for the remaining sets. If not, the user enters the desired exercise weight and repetition count for each subsequent set in step 524 before moving to step 526. If so, the logic flows directly to step 526. In step 526, the user is questioned whether she wants to enter additional exercises for the current workout. If so, the logic cycles back to step 510 in order to allow the user to select or enter the next exercise. If not, in step 528 the logic writes the new workout data to persistent storage, e.g., a memory device coupled to the separate user interface such as a hard drive of a personal computer. It is also contemplated that a user can switch among various program flow options, such as single keystroke and zero keystroke, in the setup routine, as well as enter any corresponding value required, such as the length of time for completing each set in the no-click mode.

It is further contemplated that the setup mode may incorporate a calendar and a clock for indicating that different workouts are to be performed on different days and at different times. It is also contemplated that such information can be used to provide an indication to the user, e.g., an audible chirp by the sport watch that a workout is scheduled to begin in one hour.

The program flow also preferably includes routines for modifying workout data and for analyzing such data. Specifically, a modify routine may be similar to the setup routine discussed above. However, the modify routine would advantageously permit the user to upload a pre-existing routine data from the memory of the recording device or from the separate interface, to modify its contents (e.g., exercise names, orders, set counts, intensities, etc.), and to transfer the updated information back to recording device. An analyze routine would allow the user or a trainer to view data relating to exercise parameters over a desired training phase or during any time period. It is contemplated that such visuals as graphs and charts may be used to give a user more powerful and comprehensive tools with which to analyze the data.

Figure 6:
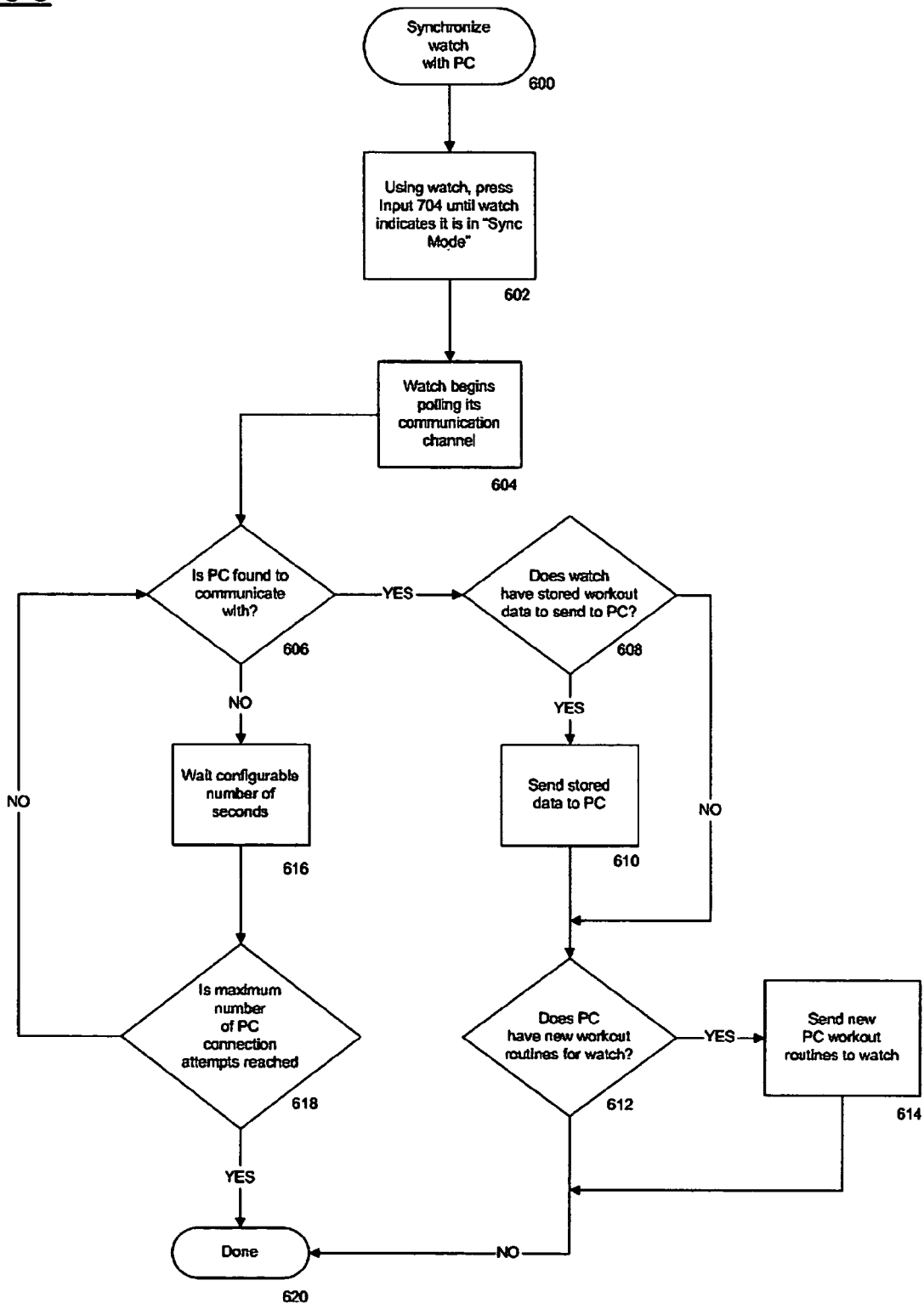

One example of a preferred program flow corresponding to the transfer of data between the recording device and a personal computer or the like is shown in FIG. 6. Means for transferring data may include, e.g., a universal serial bus, infrared technology, and/or wireless technology such as that sold under the trademark BLUETOOTH and available from a company having the trade name BLUETOOTH SIG, INC. headquartered in Overland Park, Kans. Additional communication technologies known in the art, including cellular communication technology, may be used in addition to or instead of the former. As shown in FIG. 6, a user preferably commences the data transfer by synchronizing the recording device with the personal computer in step 600. The user next presses push-button 704 until the recording device indicates "sync mode" in step 602. The recording device next begins polling its communication channel in step 604 and determines whether a personal computer is found for communication in step 606. If a computer is not found, the logic moves to step 616 where it pauses for a configurable number of seconds and then determines whether the maximum number of connection attempts, preferably also configurable, has been reached in step 618. If the maximum number has not been reached, the logic returns to step 606. If the maximum has been reached, the logic ends. If, in step 606, a personal computer or the like (an alternate terminal) is found, then the logic determines whether the recording device has any stored workout data to send to the personal computer in step 608. If so, the recording device sends the data in step 610 before moving to step 612. Otherwise, the logic skips to step 612. In step 612, the logic determines whether the personal computer has new or modified workout data for the recording device. If so, the personal computer sends that data to the recording device in step 614 before ending. Otherwise the logic immediately ends.

Figure 7:
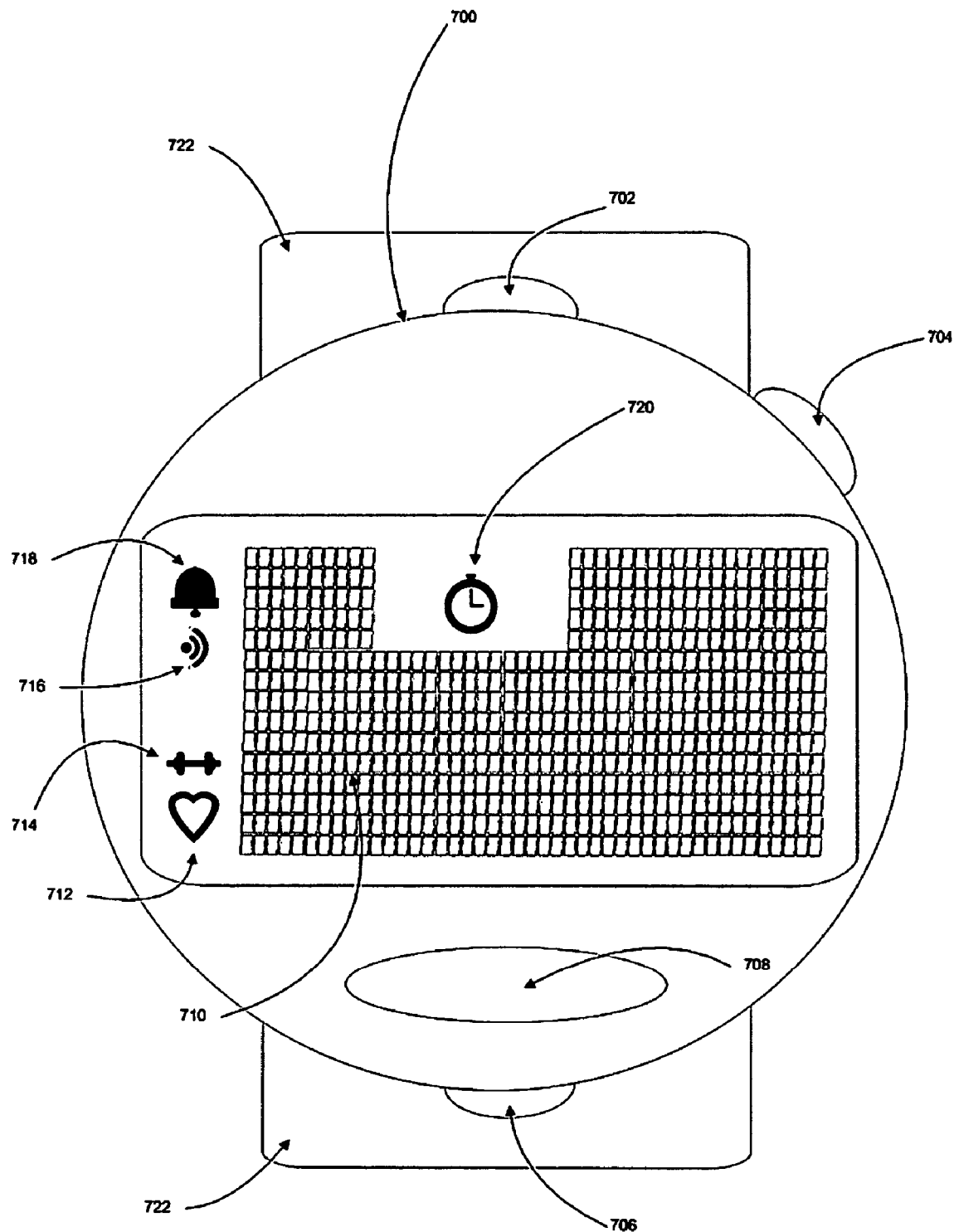
FIG. 7 is a top view of a preferred embodiment of a user interface of the present invention.

As shown in FIG. 7, the user interface 700 of a particularly preferred embodiment of the present invention, provided in a sport watch body, may be very simple and compact. The rotating device 706 is preferably a rotating crown that may be positioned along the bottom edge of the watch for easy actuation by either hand (e.g., whether the watch is fastened to the left or right arm). Alternately, input 706 may be replaced by two push-buttons or by a single push-button, e.g., for scrolling through data on the watch. Push-button 708 is preferably positioned on the top face of the watch for very easy access. A third push-button, input 704, is preferably included for moving among various modes of the program flow, including without limitation "workout mode," "sync mode," "time mode" (for a watch), "chrono mode" (for a chronograph), etc. An infrared port 702 is preferably provided for data transfer. Alternately or in addition, a universal serial bus port is preferably provided as well. The display, referenced generally by reference numeral 710, may include numbers and letters positioned in different regions thereof for easy viewing, as shown, e.g., in FIGS. 1B, 2C, and 2D. It is also contemplated that the display may include digital drawings, including animated drawings, of the exercises to be performed in order to assist those who are less experienced. Icons 712, 714, 716, 718, and 720 may be used respectively to indicate a cardiovascular mode (possibly incorporating an interconnected heart rate monitor), a resistance training mode, an audible alarm chime, an active alarm, and an active timer, respectively. The watch may be dedicated to resistance training by serving primarily the functions of a recording device for resistance training as well as those of a clock, with few if any additional functions. Alternately, the watch may incorporate and execute additional features and functions, such as the heart rate monitor. A watch band 722 is fastened to the watch body proximate the top and bottom edges of the watch body. The band 722 may comprise virtually any of the materials and any of the hooking and clasping mechanisms available, preferably in a comfortable and lightweight configuration that is gentle to the skin. It is contemplated that the watch band may be removable and may be replaced, e.g., by an alternate band to be worn on the upper arm or with a lanyard to be worn around the neck. The watch body or housing may further include a removable clip for fastening it to clothing with the band removed.

An exemplary sport watch capable of communicating with a personal computer is manufactured by a company having the trade name POLAR ELECTRO OY headquartered in Kempele, Finland and is sold under the trademark POLAR. POLAR watches generally include interconnected heart rate monitors either within the watches themselves or worn externally around the torso and connected to the watches. In contrast with the present invention, POLAR devices are instead generally used exclusively for tracking and recording time periods of cardiovascular activity (as stop-watches) and for measuring the heart rates during those time periods. However, POLAR devices are in no way capable of recording resistance training workouts, nor are they capable of use in setting up, displaying, tracking, modifying, or analyzing resistance training workouts. Physically, a POLAR sport watch generally includes an interface having from one to four inputs and having a display with a surface area of approximately one square inch, or smaller, with relatively large digital characters (numbers and letters) displayed thereon. Of particular advantage, the preferred program flow of the present invention may be incorporated into such a sport watch, allowing a simple and economical retrofit of the present invention into the existing sport watches by either replacing the circuit boards or reprogramming the existing electronic devices, and providing the additional functionality of the present invention without requiring any physical modification to the watch. In addition to the POLAR devices, other brands of sport watches that may be used include those sold under the trademark IRONMAN, manufactured in a joint venture between companies having the trade names TIMEX CORPORATION of Waterbury, Conn. and WORLD TRADE CORPORATION of Tarpon Springs, Fla.

Figure 8:
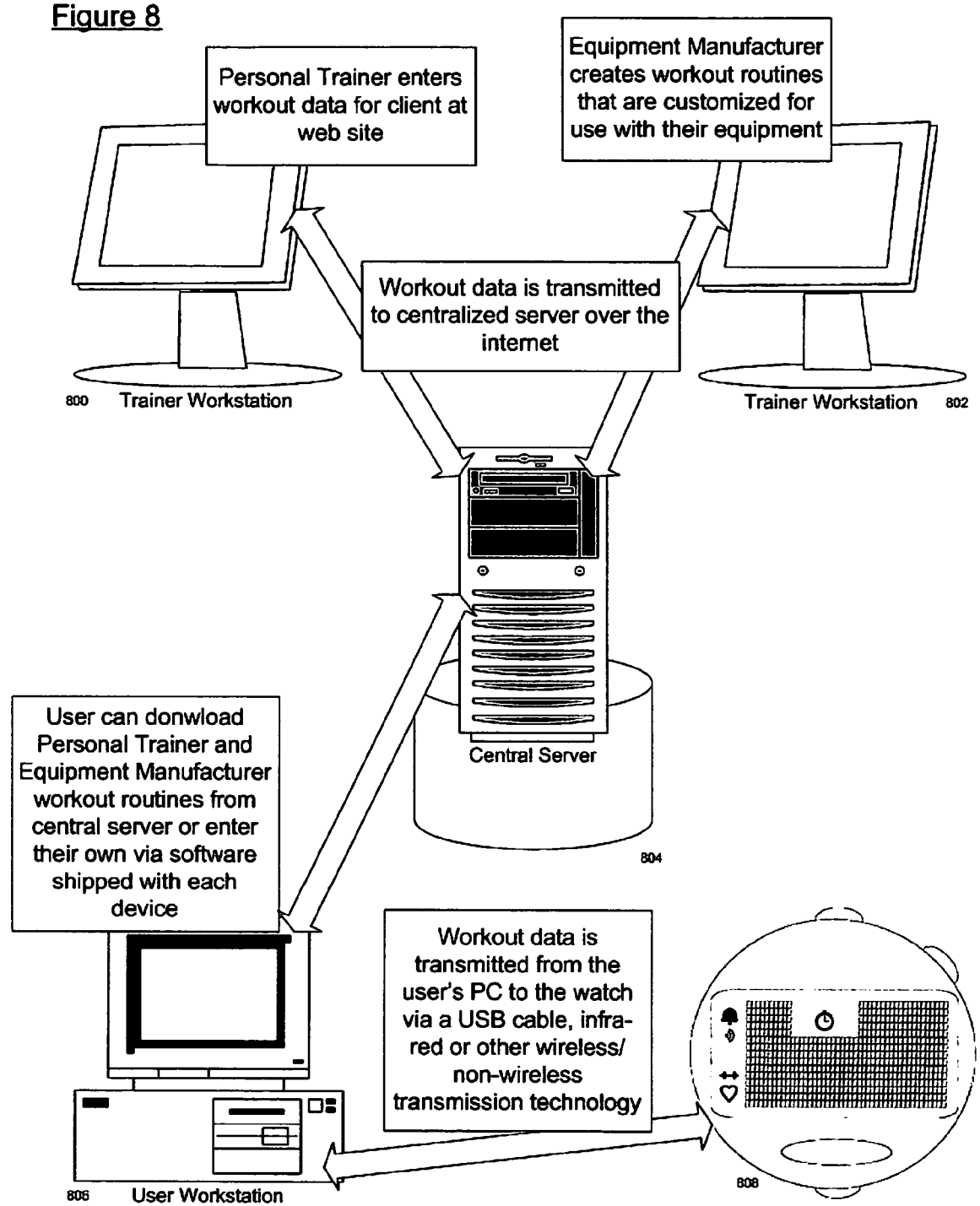
FIG. 8 is a schematic view of a preferred embodiment of an overall system for managing resistance training data.

As shown in FIG. 8, a preferred overall system for managing resistance training data may include a central server 804 providing functions analogous to those of a central hub. Data may be transferred to and from a trainer workstation 800, e.g., a personal computer or another centralized database, where a trainer (or a user) may set up, modify, and/or track resistance training data. Data may also be transferred to and from a workstation 802 on which a manufacturer of resistance training equipment or the like may create workouts specific to their equipment. An exerciser may download workout information from a personal trainer or an equipment manufacturer from the central server 804 onto a user workstation 806. The exerciser may alternately create and customize workouts with software that, e.g., may be downloaded from the internet or may be provided in a medium such as a floppy disk available together with the recording device 808. It is contemplated that any of the foregoing transmissions to and from the centralized server may be executed over the Internet. Workout data may be transmitted from the user workstation to the recording device 808 with wireless or wired transmission devices. Alternately, data may be transferred to the recording device 808 directly from the Internet and vice versa. Each recording device may comprise unique identifying means to permit a separate workstation to identify each particular device and its owner. Therefore, a single workstation may be easily maintained in a weight room of a professional team, university, or recreational fitness center for identifying and communicating with each unique recording device. Workstations in different facilities may further be interconnected through the Internet for transferring data relating to workouts and resistance training parameters in connection with each user, enabling a user to download and upload workout information in many different locations. In one embodiment, a facility needs only a personal computer with Internet access to provide the terminal. In another embodiment, no terminal at all is required because each recording device communicates directly with the Internet It can be appreciated that the overall system for managing resistance training data provides many conveniences relating to organizing the training programs of multiple clients and athletes by a single person.

While, in the foregoing, specific embodiments of the present invention have been set forth in considerable detail for the purpose of making a complete disclosure of the invention, it may be apparent to those skilled in the art that numerous changes can be made in such detail without departing from the spirit and principles of the invention.

We claim:

1. A portable recording device configured for recording achievement of resistance training objectives with at least two resistance training parameters in connection with a resistance training workout;

the device adapted to:
receive a resistance training workout comprising a series of sets for at least two different resistance training exercises, each set having resistance training objectives with at least two resistance training parameters; and record the performance of the resistance training objectives or deviations from the resistance training objectives by:

STEP A) initializing a current set as a first set from a previously received resistance training workout for a series of sets for at least two different resistance training exercises;

STEP B) presenting: a current resistance training exercise for the current set; a specified number of repetitions for the current set and a specified resistance level for the current set;

STEP C) receiving from the user a reported performance for the current set through a confirmation of performance of the specified number of repetitions at the specified resistance level for the current set;

ELSE receiving the deviation in performance of the specified number of repetitions, if any; and receiving the deviation in the specified resistance level, if any;

STEP D) IF the current set is not a last set in the previously received resistance training workout for a series of sets for at least two different resistance training exercises, THEN setting a next set in the series of previously received resistance training workout for a series of sets for at least two different resistance training exercises as the current set AND GOTO STEP B;
ELSE
the previously received resistance training workout is complete.

2. The portable recording device of claim 1 wherein:

the previously received resistance training workout may include a delay interval between a specific set and a next set; and after receiving from the user the reported performance for the current set when the current set is the specific set, timing the delay interval then at the end of the delay interval providing an indication to the user that it is time to begin the next set.

3. The portable recording device of claim 1 wherein the receiving from the user the reported performance for the current set through the confirmation of performance of the specified number of repetitions at the specified resistance level for the current set is the absence of input from the user during a window of time for the user to provide input for the current set.

* * * * *